United States Patent [19]
Klein et al.

[11] Patent Number: 5,354,200
[45] Date of Patent: Oct. 11, 1994

[54] TEMPERATURE GAUGE FOR DENTAL DRILLS AND METHOD EMPLOYING SAME

[76] Inventors: Michael Klein, 1100 Peninsula Blvd., Hewlett, N.Y. 11557; Miles J. Yacker, 285 Central Ave., Lawrence, N.Y. 11559

[21] Appl. No.: 127,014

[22] Filed: Sep. 27, 1993

[51] Int. Cl.$^5$ .................. A61C 19/04; A61C 3/02; A61C 5/00
[52] U.S. Cl. .................. 433/72; 433/165; 433/215
[58] Field of Search ............ 433/72, 104, 114, 172, 433/173, 215, 229, 165, 166; 128/736; 408/2, 6, 7, 8, 10, 11, 12; 374/170, 179

[56] References Cited

U.S. PATENT DOCUMENTS

| | | | |
|---|---|---|---|
| 3,747,085 | 7/1973 | Bala et al. | 408/6 X |
| 3,817,647 | 6/1974 | Lemelson | 408/6 X |
| 4,466,749 | 8/1984 | Cunningham et al. | 374/170 X |
| 4,480,312 | 10/1984 | Wingate | 374/170 X |
| 4,607,962 | 8/1986 | Nagao et al. | 374/170 X |
| 4,669,049 | 5/1987 | Kosednar et al. | 374/170 X |
| 4,752,770 | 6/1988 | St. Pierre | 374/179 X |
| 5,066,140 | 11/1991 | Beran | 374/179 X |
| 5,066,176 | 11/1991 | Johnstone | 408/2 X |
| 5,071,258 | 12/1991 | Usher et al. | 374/179 X |
| 5,161,922 | 11/1992 | Malloy | 408/16 X |

OTHER PUBLICATIONS

Eriksson et al., *Journal of Prosthetic Dentistry* vol. 50, No. 1, pp. 705-711, "The Effect of Heat on Bone Regeneration."
Adell et al., *International Journal of Oral Surgery*, vol. 10, pp. 387-416, "A 15-year Study of Osseointegrated Implants in the Treatment of the Edentulous Jaw."
Eriksson et al, *International Journal of Oral Surgery*, vol. 11, pp. 115-121, "Thermal Injury to Bone."
Matthews et al., *The Journal of Bone and Joint Surgery*, pp. 299-308, (1972), "Temperatures Measured in Human Cortical Bone When Drilling."
Albrektsson et al., *Journal of Periodontology*, pp. 287-396, "Osseointegrated Oral Implants: A Swedish Multicenter Study of 8139 Consecutively Inserted Nobelpharma Implants".
Albrektsson, *The Journal of Prosthetic Dentistry*, vol. 60, No. 1, Jul., 1988, "A Multicenter Report on Osseointegrated Oral Implants."
Eriksson et al, *The Journal of Prosthetic Dentistry*, vol. 50, No. 1, Jul., 1983, "Temperature Threshold Levels for Heat-induced Bone Tissue Injury: A Vital Microscopic Study in the Rabbit."
Schnitman, *Journal of the American Dental Association*, vol. 124, Apr., 1993, pp. 39-47, "Implant Dentistry: Where Are We Now?".
Jameson, *Journal of the American Dental Association*, vol. 124, p. 48 (cover page only), "Dental Implant Care: Should It Be A specialty?".
*The Temperature Handbook*, vol. 28, pp. A5-A8 (plus two unnumbered pages and cover page).
Two-page informational flyer authored by Colgate.

*Primary Examiner*—Gene Mancene
*Assistant Examiner*—Nicholas D. Lucchesi
*Attorney, Agent, or Firm*—Galgano & Burke

[57] ABSTRACT

A temperature gauge for dental drills of the type having a dental head to which a drill bur having a throughbore extending to its drill bur tip is removably mounted includes a temperature sensor receivable in the drill bur throughbore for sensing and measuring the temperature at the drill bur tip and a thermometer coupled to the temperature sensor for displaying the temperature at the drill bur tip. A method of measuring the temperature of the drill site in the jaw of a patient being fitted with a dental implant is also disclosed.

5 Claims, 2 Drawing Sheets

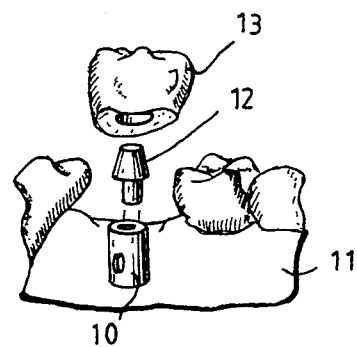
_Fig.1_
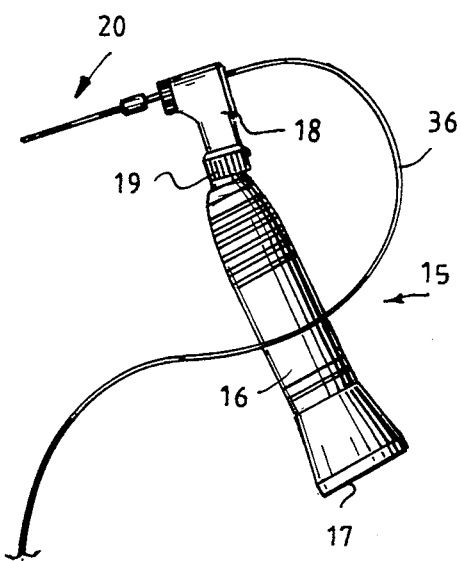
_Fig.2_
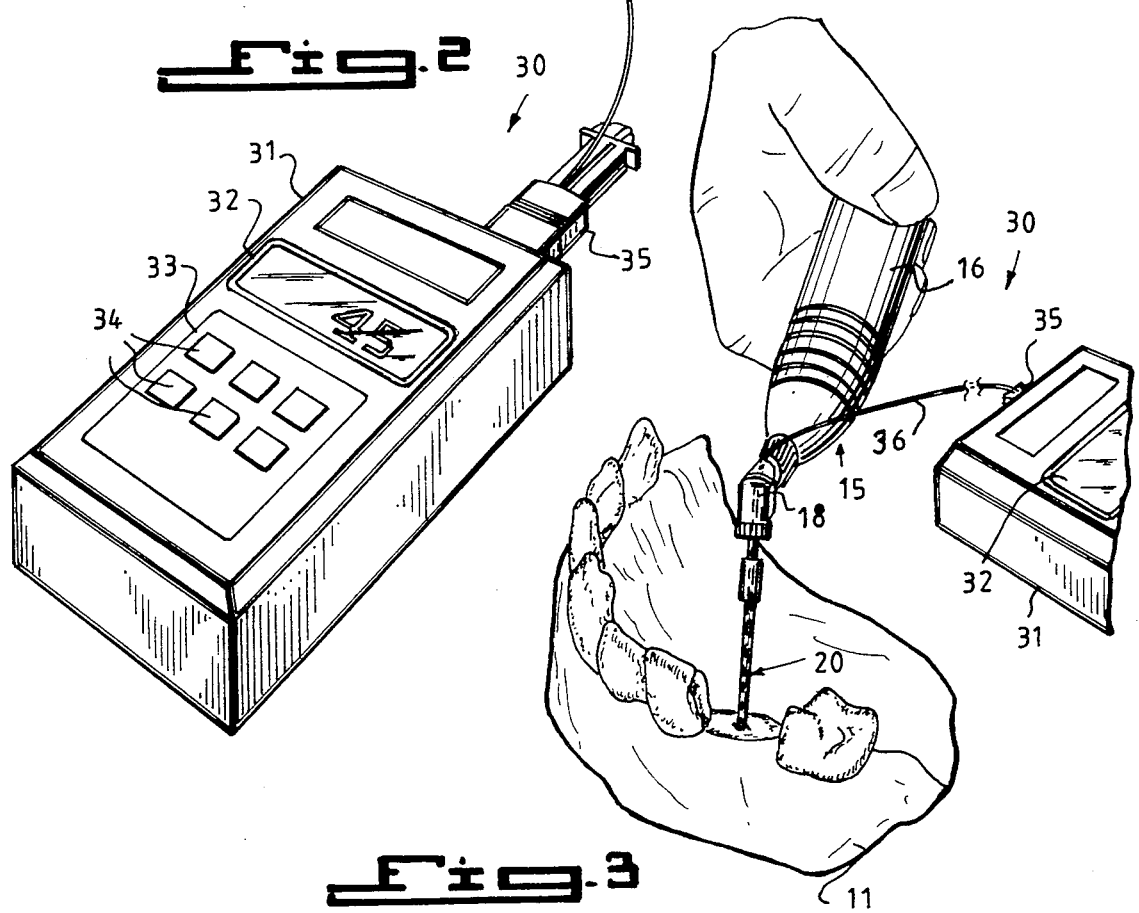
_Fig.3_

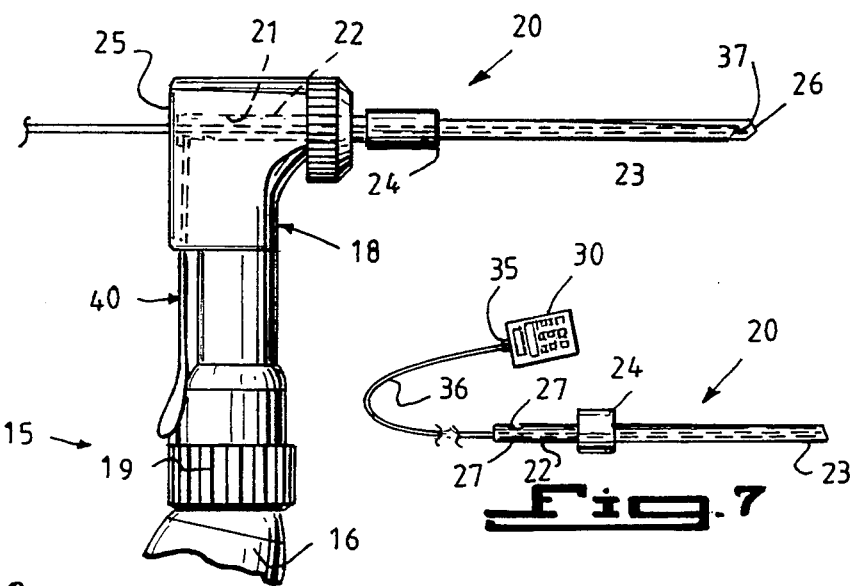
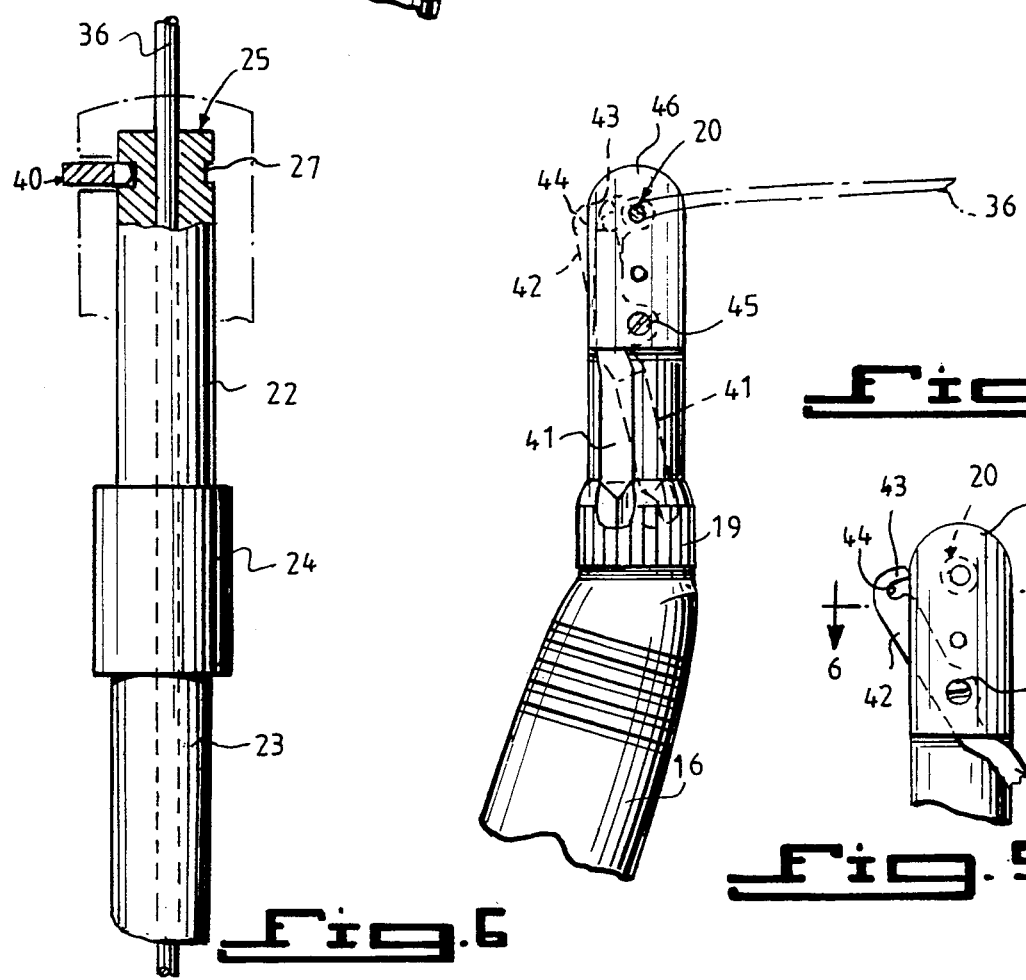

TEMPERATURE GAUGE FOR DENTAL DRILLS AND METHOD EMPLOYING SAME

BACKGROUND OF THE INVENTION

The present invention relates to a temperature gauge dental drills and to a method for employing the same More particularly, it relates to such a temperature gauge for dental drills used for dental implants.

Today, dental or intraoral implants are used throughout the world to replace missing teeth. Implants are used for: (1) anchorage of false teeth; (2) anchorage of facial prosthesis; (3) enhancement of chewing, eating and speaking; and (4) increasing patient self-esteem.

Dental implants, i.e., artificial tooth supports surgically set in the jaw, can be used to replace any number of missing teeth. Dental implants are placed into the jaw bone and allowed to heal undisturbed for a predetermined amount of time in order to assure acceptance of the implant by the body. A precise surgical placement of the implants is adhered to during placement of the implants. The implant site is prepared by the employment of a slow-speed, bone-drilling dental drill. Drill bits or burs of progressively increasing diameter are used with the drill so as to prepare the patient's jaw bone and to provide a bore site therein for the receipt of a generally cylindrical dental implant of predetermined diameter.

The surgical and drilling procedure are critical to the success of the dental implant, which requires osseointegration of the biomedical surface of the dental implant to the bone. One major cause of implant failure and rejection is attributed to overheating of the bone during implant preparation. Numerous studies have demonstrated the inability of bone cells to remain viable at temperatures above 47° C. for one minute (see, *Journal of Prosthetic Dentistry*, vol. 50, no. 1, pp. 101-107, "The Effect of Heat on Bone Regeneration"; *International Journal of Oral Surgery*, vol. 10, pp. 387-416 (1981) "A 15-year Study of Osseointegrated Implants in the Treatment of Edentulous Jaw"; and "Temperatures Measured in Human Corticobone When Drilling" and "Thermal Injury to Bone"). Consequently, it is critical to control the drilling temperature during drilling to maintain the temperature below 47° C. so as not to damage and destroy the surrounding bone cells adjacent the implant. This is presently accomplished simply by providing copious irrigation during drilling (i.e., large amounts of "cooling" water are sprayed into the drill site via the dental drill, as is well known in the art). However, to Applicants' knowledge, no device or technique is available for recording the temperature at the bone site during drilling, which enables the surgeon to be instantly aware of the drill site temperature.

Accordingly, it is an object of the present invention to provide a novel temperature gauge for dental drills and a method employing the same which records the bone temperature at the bone drilling site.

It is a further object of the invention to provide such a novel temperature gauge which is relatively simple in design, easy to use and cost effective.

It is a more particular object of the present invention to provide such a novel temperature gauge which allows the surgeon to constantly monitor any change in drill bur or bit temperature during the drilling procedure.

SUMMARY OF THE INVENTION

Certain of the foregoing and related objects are readily attained in a temperature gauge for dental drills of the type having a dental head to which a drill bur having a throughbore extending to its drill bur tip is removably mounted comprising temperature sensor means receivable in the drill bur throughbore for sensing and measuring the temperature at the drill bur tip; and thermometer means coupled to the temperature sensor means for displaying the temperature at the drill bur tip. Preferably, the temperature sensor means comprises a two-wire thermocouple probe, and the thermometer means comprises a microprocessor-based thermometer having a digital display, and the same are generally coupled together by a connector.

Certain of the foregoing and related objects are also attained in a method of measuring the temperature of the drill site in the jaw of a patient being fitted with a dental implant comprising the steps of drilling a hole in the jaw of a patient with a dental drill using drill burs of progressively increasing diameter until such time that a hole of predetermined diameter and depth is achieved, with the dental drill burs being of the type having a central throughbore extending to its drill bur tip. The temperature at the drill site is sensed, measured and monitored via temperature sensing means receivable in the drill bit throughbore and thermometer means coupled to the temperature sensor means for displaying the temperature sensed thereby. The temperature of the drill site is maintained at the tip of said drill bur below 47° C., by e.g., manually controlling the hand force or pressure applied to the drill, or the speed of drilling (including stopping and starting the same), etc., so as to prevent overheating of the bone implant site.

BRIEF DESCRIPTION OF THE DRAWINGS

Other objects and features of the present invention will become apparent from the following detailed description considered in connection with the accompanying drawings which disclose one embodiment of the present invention. It should be understood, however, that the drawings are designed for the purpose of illustration only and not as a definition of the limits of the invention.

In the drawings, wherein similar reference characters denote similar elements throughout the several views:

FIG. 1 is an exploded, perspective view showing a dental implant inserted into the jaw of a patient, to which a post and tooth cap is then secured;

FIG. 2 is a perspective view showing the temperature gauge embodying the present invention coupled to a dental drill;

FIG. 3 is a perspective view showing the temperature gauge being used during drilling of the implant site;

FIG. 4 is a fragmentarily illustrated, right side elevational view of the head of the dental drill and the thermocouple probe inserted therethrough;

FIG. 5 is a fragmentarily illustrated, rear elevational view of the head of the dental drill, showing in phantom view the unlocking of the drill bit;

FIG. 5A is a fragmentarily illustrated, enlarged, rear elevational view of the drill head showing the unlocking of the drill bit;

FIG. 6 is an enlarged, fragmentarily illustrated, side view in part section taken along line 6—6 of FIG. 5A; and FIG. 7 is a perspective view showing the drill bit coupled to the digital thermometer via the thermocouple probe.

DETAILED DESCRIPTION OF THE PREFERRED EMBODIMENT

Referring now in detail to the appended drawings, therein illustrated is a novel temperature gauge for dental drills embodying the present invention which is specifically intended for use in conjunction with the surgical and drilling procedures used for dental implants, such as the type shown in FIG. 1. As shown therein, a generally cylindrical dental implant 10 is mounted in a cylindrical cavity formed in the jaw 11 of a patient following the use of progressively increasing diameter drill bits or drill burs following the surgical and drilling procedure, as previously mentioned. Once osseointegration of the biomedical surface of the implant to the bone occurs, a post 12 is inserted into the implant which, in turn, supports an artificial tooth or cap 13 secured thereto by a dental cement or other conventional means.

FIG. 2 illustrates the conventional dental drill, generally designated by reference numeral 15, used in the dental and surgical procedure for preparing the implant site of the patient's jaw. The dental drill 15 includes a handle 16 having a lower end 17 which can be coupled in a manner well known to those skilled in the art, to a source of drive power and water for operating the drill bur with irrigation, i.e., a pressurized water stream. The top end of the handle 16 is removably attached to a dental head 18 via a screw-on neck portion 19. The dental head supports a removable dental drill bit or bur 20.

A temperature gauge embodying the present invention, generally designated 30, is coupled to the dental drill 15. The temperature gauge 30 includes a conventional microprocessor-based thermometer 31 having digital LCD display 32 and a control panel 33 containing a series of control buttons 34, as hereinafter described in detail. The digital display thermometer 31 is attached via a conventional connector 35 to a conventional insulated two-wire thermocouple probe 36. Probe 36 has an uninsulated tip which is received and positioned in the tip of the dental bur 20, as hereinafter described. This allows one to monitor the temperature at the drilling site of the jaw during the implant drilling procedure, as best illustrated in FIG. 3.

As shown in greater detail in FIG. 4, drill head 18 has a central throughbore 21, which supports the rear end portion 22 of the dental bur 20 separated from the forward portion 23 of the dental bur via a cylindrical collar 24. The dental bur 20 also has a central throughbore extending from its rear end 25 to adjacent its forward tip 26. As seen best in FIG. 6, the cylindrical rear end portion 22 of the dental bur 20 has a recessed circumferential channel 27 formed adjacent to its rear end 25 by which the dental bur is held in place in the dental head via a pivotable latch or locking arm, generally designated by reference numeral 40.

As can be seen best in FIGS. 5 and 5A, the pivotable locking arm 40 has a lower handle portion 41 and an upper locking head 42 having a hook-like clamping end 43 which has a generally U-shaped channel 44 dimensioned and configured for receipt about the cylindrical channel 27 of drill bur rear portion 22 when in a locking position. The locking arm 40 is pivotable about a central throughbore thereof held in place for pivotable movement on the locking head via a screw 45 behind a cover plate 46 of the locking head. As can be seen in the two positions shown in FIGS. 5 and 5A, by pivoting the locking arm handle 41 in a clockwise direction, the upper C-shaped clamping end 43 is pivoted behind plate 46 such that it is received within channel 27, thereby holding the dental drill bur 20 in place. By simply pivoting the locking arm handle 41 in a reverse or counterclockwise direction, the clamping end 43 will disengage from channel 27 of drill bit 20, thereby allowing the same to be removed and replaced, for example, with a drill bur of greater diameter for use during the surgical procedure.

As seen more clearly in FIGS. 4, 6 and 7, the two wire thermocouple probe 36 is inserted through the throughbore of the drill bur 20, such that its tip 37 rests adjacent the tip 26 of the drill bur. During drilling, the drill bur will rotate but, due to the sizing and dimensional difference between the thermocouple probe and the bore of the drill bur, the thermocouple probe will remain stable and stationery and will not rotate. At the same time, however, due to its close proximity to the dental bur tip 26, the probe tip 37 will be able to precisely sense the temperature at the drilling site and thereby allow monitoring of the temperature thereat.

The temperature can be readily displayed on the LCD display 32 of the digital thermometer 30 which can be positioned for ready viewing by the dental surgeon. The various control buttons 34 control the operation of the digital thermometer and can have, for example, an on/off switch, a conversion button to allow the display of either degrees Fahrenheit or degrees Centigrade, a mode switch, depending upon the type of thermocouple probe used, etc., among other features. The microprocessor thermometer itself is of conventional design and a suitable example is Model HH-21 sold by Omega Engineering, Inc. of Stamford, Conn., for their JKT type thermocouple probe. The thermocouple wire is of their K-type, according to the ANSI standard and is connected to the thermometer via a conventional connector, such as that disclosed in U.S. Pat. No. 3,914,008.

As is well known in the art, the two wire thermocouple probe is a temperature measurement sensor that consists of two dissimilar metals joined at one end (a junction) that produces a small thermo-electric voltage when the junction is heated, such as when it is placed at the drill site of the dental implant. The change in thermo electric voltage is translated by the microprocessor-based thermometer as a change in temperature, as is well known in the art. Suitable thermocouples and thermometers are disclosed in the *Omega Complete Temperature Measurement Handbook and Encyclopedia*, Volume 28, entitled "The Temperature Handbook".

In operation, the thermocouple probe 36 would be inserted into the throughbore of the drill bur 20, such that its juncture or exposed tip 37 would be at the opening of the throughbore adjacent the tip 26 of the drill bur 20. The surgeon would then begin the drilling operation and during drilling would monitor the temperature of the site on the thermometer digital display 32 to insure that the same did not rise above 47° C. During the procedure, the drill burs would be replaced with drill burs of increasing diameter until such time that a cylindrical hole was produced in the patient's jaw, which would accommodate the dental implant 10.

As can be appreciated, various modifications may be made as will be apparent to those skilled in the art. For example, other conventional temperature sensors and thermometers could be used in the present invention. In addition, may be possible to use the temperature gauge of the present invention for other surgical and dental drill procedures which require critical temperature control of the bone drill site.

Accordingly, while only one embodiment of the present invention has been shown and described, it is to be understood that many changes and modifications may be made thereunto without departing from the spirit and scope of the invention as disclosed herein.

What is claimed is:

1. A temperature gauge assembly for dental drills of the type having a dental head to which a drill bur is removably mounted comprising:
   a drill bur having a throughbore extending to a drill bur tip;
   temperature sensor means receivable in the drill bur throughbore for sensing and measuring the temperature at the drill bur tip; and
   thermometer means coupled to said temperature sensor means for displaying the temperature at the drill bur tip.

2. The temperature gauge assembly of claim 1, wherein said temperature sensor means comprises a two-wire thermocouple probe.

3. The temperature gauge assembly of claim 1, wherein said thermometer means comprises a microprocessor-based thermometer having a digital display.

4. The temperature gauge assembly of claim 3, additionally including a connector for removably coupling said thermocouple probe to said thermometer.

5. A method of measuring the temperature of the drill site in the jaw of a patient being fitted with a dental implant comprising the steps of:
   drilling a hole in the jaw of a patient with a dental drill using drill burs of progressively increasing diameter until such time that a hole of predetermined diameter and depth is achieved, said drill burs each being of the type having a central throughbore extending to a drill bur tip;
   sensing, measuring and monitoring the temperature at the drill site via temperature sensing means receivable in said drill bur throughbore of the drill bur being used in drilling and thermometer means coupled to said temperature sensing means for displaying the temperature sensed thereby; and
   maintaining the temperature of the drill site at the tip of said drill bur being used in drilling below 47° C. during said step of drilling.

* * * * *